United States Patent [19]

Holan et al.

[11] 4,309,350
[45] Jan. 5, 1982

[54] PROCESS OF MAKING PHENYLACRYLIC ESTERS

[75] Inventors: George Holan, Brighton; Reimund Walser, Box Hill, both of Australia

[73] Assignee: Commonwealth Scientific and Industrial Research Organization, Campbell, Australia

[21] Appl. No.: 115,044

[22] Filed: Jan. 24, 1980

Related U.S. Application Data

[62] Division of Ser. No. 742,575, Nov. 17, 1976, Pat. No. 4,220,591.

[30] Foreign Application Priority Data

Nov. 26, 1975 [AU] Australia ............... PC4078

[51] Int. Cl.³ ............... C07D 317/06; C07C 101/00; C07C 79/46; C07C 69/76
[52] U.S. Cl. ............... 260/340.5 R; 560/9; 560/19; 560/20; 560/45; 560/47; 560/55; 560/104
[58] Field of Search ............... 560/104, 55, 9, 20, 560/23, 45, 47, 19; 260/340.5 R

[56] References Cited

U.S. PATENT DOCUMENTS 3,442,935  5/1969  Pine ........................ 260/55
3,803,254  4/1974  Hattori et al. .............. 260/55
3,804,899  4/1974  Ebnother et al. ............ 260/55

FOREIGN PATENT DOCUMENTS 655700  8/1979  U.S.S.R. .................... 560/55

Primary Examiner—Paul J. Killos

Attorney, Agent, or Firm—Bacon & Thomas

[57] ABSTRACT

The (+), (−) and (±) forms of the compounds of formula I

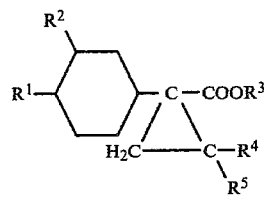

wherein
$R^1$ is hydrogen or a methoxy, ethoxy, propoxy, methylthio, ethylthio, propylthio, fluoro, chloro, bromo, methyl, ethyl, nitro or amino group, and
$R^2$ is a hydrogen or methyl group or $R^1$ and $R^2$ together form a methylenedioxy group;
$R^3$ is hydrogen, or a lower alkyl group, or one of the following groups (a) to (d):
  (a) m-phenoxybenzyl,
  (b) 2-benzyl-4-furylmethyl
  (c) α-cyano-m-phenoxybenzyl
  (d) 3-4-methylenedioxy-benzyl,
and $R^4$ and $R^5$ are the same or different groups and each is a fluoro, bromo, chloro or methyl group.

The compounds of formula I in which $R^3$ is one of groups (a) to (d) are extremely active as insecticides (except when $R^1$ is an amino group). The compounds also possess the property of contact repellency to insects.

10 Claims, No Drawings

PROCESS OF MAKING PHENYLACRYLIC ESTERS

This is a division of application Ser. No. 742,575, filed Nov. 17, 1976, U.S. Pat. No. 4,220,591.

This invention relates to new insecticidal compounds, methods for preparing these compounds and to new insecticidal compositions containing the compounds.

Throughout this specification, where the context permits, the word "insect" is used in its broad common usage and includes spiders, mites, nematodes and other pests which are not classed as insects in the strict biological sense. Thus the term implies reference not only to those small invertebrate animals belonging mostly to the class Insecta, comprising six-legged, usually winged forms, such as beetles, bugs, flies and the like, but also to other allied classes of arthropods whose members are wingless and usually have more than six legs, such as spiders, wood lice and the like, and especially to the order Acaridae which includes the mites and ticks. The words "insecticide" and "insecticidal" are similarly used.

The compounds provided by this invention have the general formula I

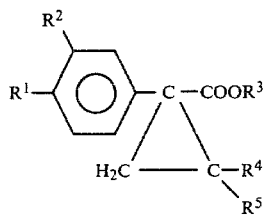

wherein $R^1$ is hydrogen or a methoxy, ethoxy, propoxy, methylthio ethylthio, propylthio, fluoro, chloro, bromo, methyl, ethyl, nitro or amino group, and $R^2$ is a hydrogen or methyl group or $R^1$ and $R^2$ together form a methylenedioxy group;

$R^3$ is hydrogen, or a lower alkyl group, or one of the following groups (a) to (d):

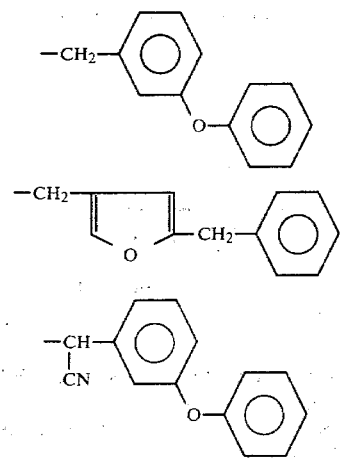

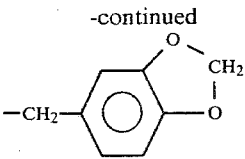

and $R^4$ and R are the same or different groups and each is a fluoro, bromo, chloro or methyl group.

Known compounds which can be regarded as related to the compounds of formula I are those in which the groups (a) to (c) are present as esterifying groups with chrysanthemic acid in commercial pyrethroids. The acid of the present invention (formula I, $R^3=H$) and its esters are novel.

The compounds of formula I in which $R^3$ is one of groups (a) to (d) are extremely active as insecticides, except when $R^1$ is an amino group, having an insecticidal activity an order of magnitude greater than most known insecticides. These compounds also possess the property of contact repellency to insects.

The compounds of formula I in which $R^1=NH_2$ are useful as intermediates in the preparation of compounds with $R^1=$ other chemical groups as shown in Example J, but are not active as insecticides.

The compounds of formula I in which $R^3=H$ or lower alkyl are useful as intermediates in the preparation of the other esters with $R^3=$(a) to (d) as shown below.

The compounds of formula I are optically active and can be resolved into their optical isomers by conventional methods. The invention thus includes the individual optical isomers of the compounds as well as the racemic forms.

It should also be noted that the insecticidal activities of optical isomers of the compounds I ($R^3=$(a) to (d)) may differ by an order of magnitude or more. The (−) form (shown by x-ray diffraction to be of —S— configuration) is always more active than the (+) form.

The invention also includes methods for the synthesis of the compounds I.

The compounds I in which $R^3$ is one of the groups (a) to (d) may be prepared by esterification of the free acid (formula I, $R^3=H$) with the appropriate alcohol $R^3OH$, where $R^3$ is one of the groups (a) to (d). Such esterification may be carried out by any suitable known method, e.g., by direct reaction or by prior conversion of the acid and/or the alcohol to a suitable reactive derivative, or by an ester interchange reaction between the alcohol $R^3OH$ ($R^3=$(a) to (d)) and a lower alkyl ester of the acid.

The acid (formula I, $R^3=H$) is prepared (as its ethyl ester) by free radical addition of the carbene :$CR^4R^5$ (where $R^4$ and $R^5$ are as defined above) to the substituted phenylacrylic ester of formula II

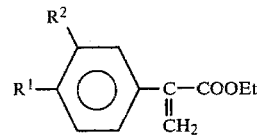

where $R^1$ and $R^2$ are as defined above.

The esters II may be obtained according to the following general procedure:

(1) The appropriately substituted phenylacetic ester (V) is condensed with a di(lower alkyl)oxalate in the presence of a basic catalyst, to produce a sodium enolate salt (IV).

(2) The solution of the enolate salt is acidified to give the corresponding phenyloxaloacetate (III).

(3) The compound III is reacted with formaldehyde under alkaline conditions to give the phenyl hydroxymethyl acetate which on dehydration (spontaneously) yields the phenylacrylic ester (II).

This reaction sequence is illustrated in the following overall reaction scheme. It will be appreciated that the specific acids and bases indicated may be replaced by other suitable compounds. Also lower alkyl esters, other than the ethyl esters shown may be employed.

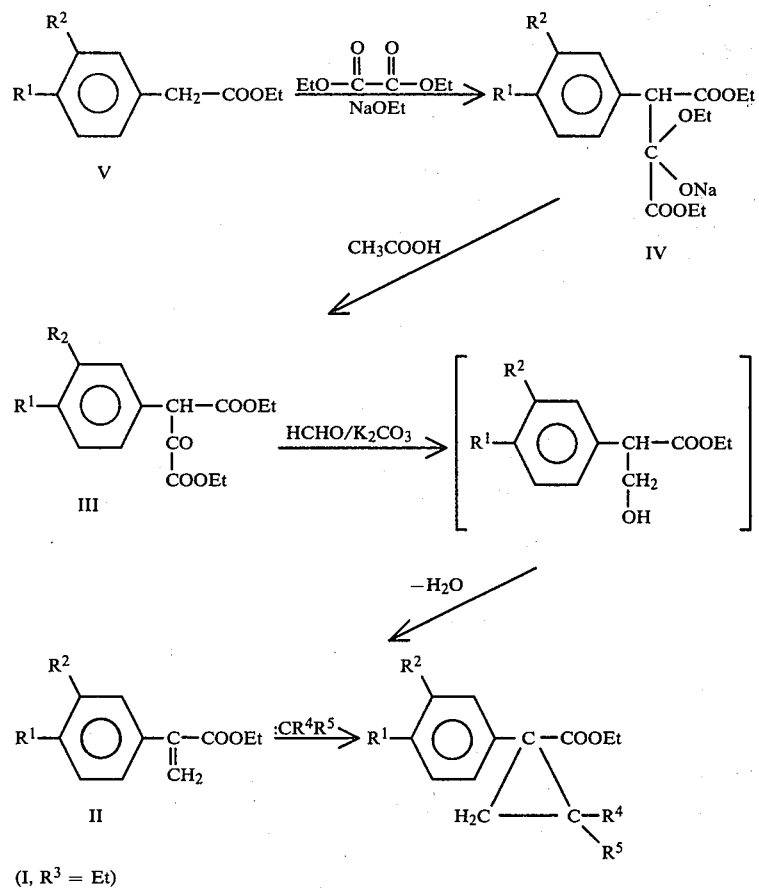

(I, $R^3$ = Et)

The radical $:CR^4R^5$ may be generated from one of the following sources (i) Where $R^4=Cl$ and $R^5=F$, Cl or Br; by reaction of the appropriate haloform $HCR^4{}_2R^5$ or $HCR^4R^5{}_2$ with alkali in the presence of a phase transfer catalyst, e.g. triethylbenzylammonium chloride

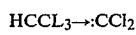

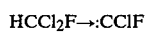

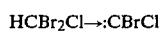

(ii) Where $R^4=R^5=F$ or Cl; from $CF_2Cl\text{-}COONa$ or $CCl_3\text{-}COONa$ respectively.

(iii) Where $R^4=R^5=CH_3$; from

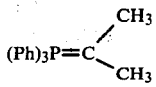

The general approach to formation of the esters of the invention is as follows:

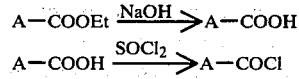

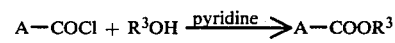

where A is

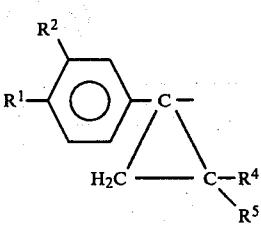

$R^1$, $R^2$, $R^4$ and $R^5$ are as defined above and $R^3$ is one of the groups (a) to (d) defined above.

Alternatively the ethyl ester can be directly converted as follows:

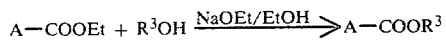

The phenyl acrylic acids (formula II) can also be prepared, in a lower yield, by a method derived from that of G. Schwenker, H. Meyer, and S. Strauss, Arch. Pharmac., 305, 839 (1972) which consists of reacting the corresponding ester of phenylacetic acid with paraformaldehyde in dimethyl sulphoxide in the presence of sodium alkoxide. The α-hydroxymethylated phenyl acetic acid ester thus prepared is stable but we have found that it can be dehydrated to the acrylate. (The latter step was not reported in the publication.)

In a modification of the general method described above the phenyl acrylic ester II can be converted into the ester IIa by any suitable procedure

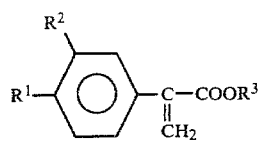

where $R^3$ is one of groups (a) to (d).

The ester IIa is then reacted with the carbene $:CR^4R^5$ to give the required compound of formula I.

The compounds of formula IV as stated above are also novel and form a part of this invention.

The new compounds described herein may be incorporated in a suitable inert solvent, or mixture of solvents, or in a solid mixture, with or without other substances, such as wetting, dispersing and sticking agents. The compounds may be employed in such compositions either as the sole toxic agent or in combination with other insecticides such as pyrethrum, rotenone, or with fungicidal or bactericidal agents, to provide compositions useful for household and agricultural dusts and sprays, textile coating and impregnation, and the like. The compounds may be dissolved in suitable organic solvents to provide solutions of enhanced utility. The new compounds may also be placed in aqueous suspension by dispersing organic solvent solutions of the compounds in water. The new compounds may also be mixed with an inert, finely divided, solid diluent or carrier. The insecticidal compounds may be admixed in their original forms or in solution. The new compounds are active against injurious insects of many kinds, such as moths, mosquitoes, flies, beetles and others.

In particular, the compounds of the invention may be advantageously combined with other substances which have a synergistic or potentiating action. Generally such substances are of the class of microsomal oxidase inhibitors i.e. they inhibit the detoxification of insecticides in insects produced by the action of oxidative enzymes. Typical substances of this type are the pyrethrin synergists of which the following are examples:

| Common Name | Chemical Name |
| --- | --- |
| Piperonyl butoxide | α-[2-(2-butoxyethoxy)ethoxy]-4,5-methylenedioxy-2-propyltoluene |
| Piperonyl cyclonene | 3-hexyl-5(3,4-methylenedioxyphenyl)-2-cyclohexanone |
| "Sesoxane" (Sesamex) | 2-(3,4-methylenedioxy-phenoxy)-3,6,9-trioxaundecane |
| "Sulfoxide" | 1,2-(methylenedioxy)-4-[2-(octyl-sulfinyl)propyl]-benzene |
| n-Propyl isome | dipropyl-5,6,7,8-tetrahydro-7-methylnaphtho-[2,3-d]-1,3-dioxole-5,6-dicarboxylate |

("Sesoxane", "Sesamex" and "Sulphoxide" are Registered Trade Marks).

We have found that 'Sesoxane' (made by Shulton Inc., Clifton, N.J., U.S.A.) is particularly useful as a potentiator. The amount of 'Sesoxane' used may vary from 1/1000th to five times the weight of the compound I the preferred range being from about 1/100th to an equal part by weight. Piperonyl butoxide also is a useful potentiator in similar amounts.

The preparation and properties of the compounds of the invention are illustrated by the following specific examples. It should be noted, of course, that these examples are intended to be illustrative of the methods and procedures utilized in preparing the compounds and that they are not intended to be restrictive or to be regarded as embodying the only way in which the compounds can be formed and recovered.

All temperatures are in Celsius.

EXAMPLE A

The following example shows the general method of forming the 2-aryl-acrylic acid esters (Formula II).

Ethyl-2-(p-ethoxyphenyl)-acrylate

Alcohol-free sodium ethoxide freshly prepared from sodium (13.9 g) and excess ethanol was slurried in dry benzene (200 ml). To this suspension diethyl oxalate (88.5 g) was added over 15 minutes. Ethyl-p-ethoxyphenyl-acetate (V) (114.2 g) was added to the resulting clear yellow solution over 30 minutes at room temperature. After a further 1 hour period the reaction mixture solidified. The solid, sodium diethyl-2-p-ethoxyphenyl-3-ethoxy-3-oxido-oxaloacetate (IV) was triturated and washed well with ether. The combined ether washings were evaporated to a small volume to obtain a second crop of the salt.

The combined yield was 227.4 g.

The sodium salt was acidified by adding it in portions to a well stirred emulsion of equal parts of diethyl ether and dilute acetic acid (approximately 10%). After separation the ether layer was washed with water and dilute sodium bicarbonate solution, and dried with anhydrous sodium sulphate. After evaporation of the ether, the resulting oil was crystallized from petroleum ether (b.p. 60°–80°), to yield diethyl-2-p-ethoxyphenyl-oxaloacetate (III) 143.8 g (85%), m.p. 59°–60°.

The keto-ester III (143.8 g) was stirred in dilute formaldehyde solution (62 ml 37% formaldehyde+water 220 ml) and to the suspension potassium carbonate solution (54.5 g, in water 280 ml) was added dropwise. At the end of the addition, ether was added to the stirred suspension to dissolve the gummy precipitate which formed and after an additional 15 minutes, gas evolution commenced. When this gas evolution ceased (after about 2 hours) the reaction mixture was extracted with additional ether and the combined ether extracts were washed with water and evaporated after drying with $Na_2SO_4$. The yield of the ethyl-2-(p-ethoxyphenyl)acrylate (II) (isolated as a yellow oil) was 97.8 g (79.8%).

The following examples B to F show the general method of forming the 2-arylcyclopropane esters and acids (formula I, $R^3$=Et and H)

EXAMPLE B

Ethyl-1-p-ethoxyphenyl-2,2-dichloro-1-cyclopropane carboxylate (formula I, $R^3$=Et).

Ethyl-2-p-ethoxyphenyl acrylate (22.0 g) chloroform (23.9 g) and triethylbenzylammonium chloride (0.2 g, dissolved in ethanol, (0.4 ml)) were stirred together under argon cover. Sodium hydroxide (50 ml 50% w/w solution) was added to the solution over 10 minutes, and the temperature allowed to rise to 40°. The mixture was allowed to react without external cooling for a further 3 hours, methylene chloride being aded to facilitate the stirring of the thick slurry. The reaction mixture was quenched with ice water (200 ml), extracted with methylene chloride and washed consecutively with water, dilute hydrochloric acid, water and finally dried over anhydrous sodium sulphate. After evaporation of the solvent the oil was distilled at 80°–90° at $1 \times 10^{-6}$ Torr. The yield of the ethyl ester (formula I, $R^3$=Et) was 24.65 g.

EXAMPLE C 1-p-Ethoxyphenyl-2,2-dichlorocyclopropane-1-carboxylic acid (formula I, $R^3$=H)

The ethyl ester (24.65 g) was hydrolysed by refluxing for 1 hour with 1 N sodium hydroxide with ethanol added to the reaction mixture, to form a homogeneous solution. The ethanol was evaporated under vacuum, the solution neutralized with dilute HCl and after carbon treatment cooled in ice.

The acid crystallized in pure state from the solution. Yield 21.8 g (79.5%) m.p. 135°–7°.

EXAMPLE D

Ethyl-1-p-ethoxyphenyl-2,2-dimethylcyclopropane-1-carboxylate

Isopropyl-triphenyl-phosphonium iodide (10.8 g) was suspended in dry tetrahydrofuran under argon cover at room temperature. To this suspension was added n-butyl lithium (18 ml of 1.42 M solution in hexane) over 5 minutes. After stirring for an additional 30 minutes, ethyl-2-p-ethoxyphenyl-acrylate (5.51 g) in tetrahydrofuran (50 ml) was added dropwise to the deep red solution while maintaining the temperature between 22°–30°. After the exothermic reaction had subsided the solution was stirred at room temperature for 16 hours. The reaction mixture was then quenched in ice-water and extracted with ether. After washing and evaporation of the ether layer the resulting oil was distilled at 90° ($1 \times 10^{-6}$ Torr.) The oil, $n_D^{24}$=1.5198, was hydrolysed to the acid without further purification.

EXAMPLE E 1-p-Ethoxyphenyl-2,2-dimethylcyclopropane-1-carboxylic acid

The ester was refluxed for 6 hr in a solution of KOH (10 g) in ethanol/water mixture (150 ml 50%). The ethanol was evaporated off and the solution extracted with ether. The aqueous layer was acidified to yield 5.1 g of the pure acid; m.p. 104°–5°.

EXAMPLE F 1-p-Ethoxyphenyl-2,2-difluorocyclopropane-1-carboxylic acid

Ethyl-2-p-ethoxyphenyl acrylate (11.0 g) was heated in sulfolane (50 ml) to 160°–170°. To this solution dry sodium chlorodifluoroacetate (15.3 g) was added in portions over 1 hour. After a further 30 minutes, the solution was quenched in ice-water and extracted with methylene chloride. The oily residue obtained after the evaporation of the solvent was distilled at 60°–70° ($1 \times 10^{-4}$ torr.) to yield 6.05 g of the ester as a yellow oil.

The ester (5.4 g) was hydrolysed in NaOH (2 N) ethanol solution to yield 5.2 g of the acid m.p. 82°–3° from pet. ether/$CH_2Cl_2$.

EXAMPLE G

This example shows the general method of formation of esters of 1-p-ethoxyphenyl-2,2-dichlorocyclopropane-1-carboxylic acid (formula I, $R^3$=(a) to (h)).

(a)

1-p-Ethoxyphenyl-2,2-dichlorocyclopropane-1-carbonyl chloride

The 1-p-ethoxyphenyl-2,2-dichlorocyclopropane-1-carboxylic acid (1.38 g) was refluxed on a water bath with thionyl chloride (1.19 g) for 15 minutes. The excess thionyl chloride was then evaporated under vacuum (1 Torr.) and the residue of carbonyl chloride reacted without further purification with one of the alcohols (a), (b), (c) or (d).

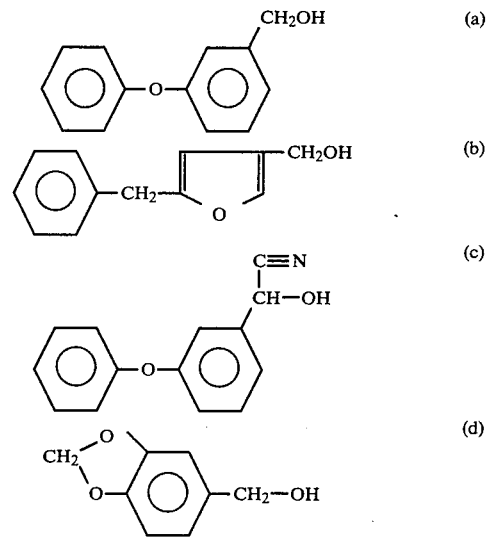

(b) Formation of Esters

The alcohol and pyridine in molar ratio 1:1.5 in 5 times their volume of benzene were added to the acid chloride (1 molar ratio dissolved in 5 times its volume of petroleum ether (b.p. 60°–80°). The mixture was allowed to react over 10 hr and after evaporation of the solvents the product was either distilled under vacuum or crystallized from petroleum ether.

EXAMPLE H

This example shows the method of preparing the m-Phenoxy-α-cyanobenzyl esters, i.e., where $R^3$ is the m-phenoxy-α-cyanobenzyl radical (c).

Potassium cyanide (1.30 g) dissolved in water (5 ml) was added in portions to m-phenoxybenzaldehyde bisulphite salt (3.02 g). Ether (5 ml) was then added and the gummy precipitate stirred to form a fine dispersion. This dispersion was stirred for a further 3 hours. The reaction mixture was then extracted with ether and the ether extract washed consecutively with water, sodium bisulphite solution, Na$_2$CO$_3$ solution, water and dried over anhydrous Na$_2$SO$_4$. The cyanohydrin (2.16 g; yellow oil) was reacted immediately, without further purification, with the respective acid chloride by the method of Example G.

EXAMPLE I

Resolution of the optical isomers of 1-p-ethoxyphenyl-2,2-dichlorocyclopropane-1-carboxylic acid To the racemic acid (3 g) (+)-α-methylbenzylamine (1.5 ml) in ethyl acetate (25 ml) was added and the solution heated to 40°. On standing for 4 days 3.82 of solid precipitate of (+)benzylamine-(−) acid salt was collected. This was recrystallized from ethyl acetate (90 ml) followed by recrystallization from a smaller amount (50 ml) of the same solvent, followed by acetone (25 ml). The crystallizations were carried out at 24 hours intervals, at room temperature (19°–23°). The last recrystallization yielded white needles of the (−)acid salt, 0.68 g, m.p. 172°.

The (−)acid salt was dissolved in ethanol and HCl (2 N) was added. The crystalline precipitate that formed in 24 hours was washed with water and recrystallized twice from aqueous ethanol. The (−)acid 0.38 g (m.p. 167°) had specific rotation $\alpha_D = -91.8$ measured on a Zeiss recording polarimeter in a 2 cm cell at 13°.

To the combined filtrates from the isolation of the (−)acid salt, hydrochloric acid was added and the isolated impure (+)acid was treated with (−)-α-methyl benzylamine (1.5 ml) in ethyl acetate (20 ml). The solution was evaporated to dryness and the solid residue (1.5 g) crystallised from ethyl acetate in 48 hours to yield needles (0.60 g), m.p. 173°. The (+)acid was obtained from this salt by treatment with methanolic HCl. The (+)acid was recrystallized from aqueous ethanol (0.38 g) m.p. 167°. The specific rotation ($\alpha_D$) was +91.0 measured at 13°.

The optically active m-phenoxybenzyl esters were prepared from the resolved acids by methods described for the racemic acid.

The (−)acid ester had a specific rotation $\alpha_D = -30.5$ while the (+)acid ester had $\alpha_D = +30.5$ measured at 13°.

EXAMPLE J m-phenoxybenzyl-1-p-bromophenyl-2,2,-dichlorocyclopropane carboxylate (formula I,R$^1$=Br) from m-phenoxybenzyl-1-p-aminophenyl-2,2-dichlorocyclopropane carboxylate (formula I,R$^1$=NH$_2$)

m-phenoxybenzyl-1-p-aminophenyl-2,2-dichlorocyclopropane carboxylate (4.28 g) was added with stirring to a solution of 40% hydrogen bromide (5.87 ml) in glacial acetic acid (10 ml) and cooled to 10°. It was diazotised by addition of sodium nitrite (0.7 g). To this solution copper flakes (0.3 g) were added and the temperature allowed to rise slowly to room temperature overnight. The black oil which separated was taken up in dichloromethane and ice water. The resulting layers were separated and the aqueous layer was twice extracted with dichloromethane. The dichloromethane extracts were combined, washed with water then dilute sodium bicarbonate solution then water and dried over anhydrous sodium sulphate. The dichloromethane was removed by evaporation and the resulting oil was purified by chromatography on a silica column with dichloromethane as eluent.

4.30 g (yield 87%) of a pale yellow viscous oil was recovered from the purification.

EXAMPLE K

This example demonstrates the preparation of α-hydroxymethylated phenyl acetic acids by the method of Schwenker, Meyer and Strauss, and their subsequent dehydration and hydrolysis to phenyl acrylic acids which can be used as before to prepare cyclopropane carboxylic acids.

Ethyl-2-p-ethoxyphenyl-3-hydroxypropionate

Sodium ethoxide solution in ethanol (0.5 M, 18 ml) was added to a solution of ethyl-p-ethoxyphenylacetate (30 g) in dry dimethyl sulphoxide (180 ml) under argon cover. The mixture was stirred for 5 minutes and dry paraformaldehyde (5.4 g) added. After 19 h stirring, acetic acid (1.5 ml) was added, the solution quenched in ice and extracted with ether. The ether layer was washed with sodium bicarbonate solution and water, dried over anhydrous sodium sulphate, and the solvent evaporated. The resulting oil crystallized from petroleum ether (40°–60°) to yield 27.8 g product, m.p. 35°–35°.

Analysis: found C, 65.28; H, 7.52. C$_{13}$H$_{18}$O$_4$ requires C, 65.53; H, 7.61.

2-p-Ethoxyphenyl acrylic acid

The ethyl-2-p-ethoxyphenyl-3-hydroxypropionate (0.7 g) was refluxed for 7 h in potassium hydroxide solution (20%, 2 ml). It was acidified with dilute HCl and the crude acid (0.46 g, m.p. 103°–107°) used for the next step without further purification.

1-p-Ethoxyphenyl-2,2-dibromocyclopropane carboxylic acid

The acrylic acid (0.29 g) was reacted with sodium hydroxide (50%, 1 ml) and bromoform using triethylbenzyl ammonium chloride as a catalyst following the method of Example B. After isolation 0.16 g of product identical to authentic material obtained by hydrolysis of the ester of Example 7 Table I, was obtained.

EXAMPLES 1 to 37

Using the general methods illustrated in Examples A to J, the compounds shown in Table I were prepared. Analytical and other identifying data are given in Table I.

TABLE I

| No. | R₁ | R₂ | R₃ | R₄ | R₅ | ANALYSIS* FOUND C | H | Cl | F(Br) | CALCULATED C | H | Cl | F(Br) | Bp (press.) °C. torr | m.p. °C. | NMR* δ(ppm) | Ir ν$_{max.}$ (cm⁻¹) —COOR |
|---|---|---|---|---|---|---|---|---|---|---|---|---|---|---|---|---|---|
| 1 | Cl | H | C₂H₅ | Cl | Cl | 49.3 | 3.89 | 36.9 | | 49.1 | 3.77 | 36.2 | | 95 (1 × 10⁻⁶) | | | |
| 2 | Cl | H | H | Cl | Cl | 45.4 | 2.72 | 40.0 | | 45.2 | 2.66 | 40.1 | | | 111 | | |
| 3 | C₂H₅O | H | C₂H₅ | Cl | Cl | 55.8 | 5.32 | 23.7 | | 55.5 | 5.32 | 23.4 | | 80–90 (1 × 10⁻⁶) | | | |
| 4 | —OCH₂O— | | C₂H₅ | Cl | Cl | 51.2 | 4.04 | 23.2 | | 51.5 | 3.99 | 23.4 | | | 137 | | |
| 5 | —OCH₂O— | | H | Cl | Cl | 48.0 | 2.99 | 25.8 | | 48.0 | 2.93 | 25.8 | | | 74 | | |
| 6 | C₂H₅O | H | C₂H₅ | Br | Br | 42.6 | 4.42 | | (40.5) | 42.9 | 4.11 | | (40.8) | | 161 | | |
| 7 | C₂H₅O | H | H | Br | Br | 39.8 | 3.42 | | (43.7) | 39.6 | 3.32 | | (43.9) | 90 (1 × 10⁻⁴) | | | |
| 8 | C₂H₅O | H | C₂H₅ | F | F | 62.3 | 5.96 | | 13.7 | 62.7 | 5.97 | | 14.1 | 60 (1 × 10⁻⁴) | 142 | | |
| 9 | C₂H₅O | H | H | F | F | 59.4 | 5.02 | | 15.9 | 59.5 | 4.09 | | 15.7 | | 81 | | |
| 10 | Cl | H | A | Cl | Cl | 61.8 | 3.00 | 23.8 | | 61.7 | 3.92 | 23.9 | | 155 (1 × 10⁻⁶) | | quartet, 2.33 | 1735 |
| 11 | Cl | H | B | Cl | Cl | 60.8 | 4.10 | 24.6 | | 60.6 | 3.93 | 24.4 | | | 51 | quartet, 2.35 | 1745 |
| 12 | C₂H₅O | H | A | Cl | Cl | 66.1 | 5.00 | 15.4 | | 66.6 | 4.85 | 15.5 | | | | quartet, 2.30 | 1738 |
| 13 | C₂H₅O | H | B | Cl | Cl | 64.9 | 5.22 | 16.2 | | 64.7 | 4.98 | 15.9 | | | | quartet, 2.33 | 1735 |
| 14 | —OCH₂O— | | A | Cl | Cl | 63.1 | 3.97 | 15.5 | | 63.0 | 3.95 | 15.5 | | | 58 | quartet, 2.35 | 1727 |
| 15 | —OCH₂O— | | B | Cl | Cl | 62.0 | 4.12 | 15.9 | | 62.0 | 4.07 | 15.6 | | | 45 | quartet, 2.30 | 1730 |
| 16 | C₂H₅O | H | A | Br | Br | 54.9 | 4.08 | | (29.3) | 55.0 | 4.06 | | (29.3) | | | quartet, 2.47 | 1740 |
| 17 | C₂H₅O | H | B | Br | Br | 54.2 | 4.15 | | (29.5) | 54.0 | 4.15 | | (29.9) | | | quartet, 2.45 | 1735 |
| 18** | (−)C₂H₅O | H | A | Cl | Cl | same as No. 13 | | | | | | | | | | | |
| 19** | (+)C₂H₅O | H | A | Cl | Cl | same as No. 13 | | | | | | | | | | | |
| 20 | C₂H₅O | H | A | F | F | 71.1 | 5.22 | | 9.0 | 70.7 | 5.27 | | 9.0 | | | multiplet, 2.21 | 1740 |
| 21 | C₂H₅O | H | B | F | F | 70.3 | 5.38 | | 9.1 | 68.9 | 5.44 | | 9.2 | | | multiplet, 2.24 | 1738 |
| 22 | C₂H₅O | H | A | Cl | CH₃ | | | 14.7 | | 64.7 | 4.4 | 14.7 | (N;2.9) | | | quartet, 2.33 | 1750 |
| 23 | C₂H₅O | H | B | Cl | CH₃ | | | 14.7 | | 62.3 | 3.55 | 14.7 | (N;2.9) | | | quartet, 2.32 | 1750 |
| 24 | —OCH₂O— | | C | Cl | Cl | | | | | | | | | | | | |
| 25 | C₂H₅O | H | A | CH₃ | CH₃ | 78.1 | 6.93 | — | (O;15.1) | 77.9 | 6.77 | | (O;15.4) | | | quartet, 1.38 | 1730 |
| 26 | C₂H₅O | H | B | CH₃ | CH₃ | 77.1 | 6.77 | — | (O;15.7) | 77.2 | 6.98 | | (O;15.8) | | | quartet, 1.38 | 1730 |
| 27 | C₂H₅O | H | D | Cl | Cl | 58.62 | 4.36 | 17.7 | — | 58.69 | 4.43 | 17.3 | | | | quartet, 2.32 | 1735 |
| 28 | CH₃O | H | A | Cl | Cl | 67.64 | 4.76 | 8.4 | 4.7 | 67.53 | 4.72 | 8.3 | 4.5 | | | multiplets 2.7, 1.9 | |
| 29 | C₂H₅O | H | A | Br | Cl | 60.21 | 4.60 | 7.2 | (16.2) | 59.84 | 4.42 | 7.1 | (15.9) | | | doublets 2.58, 2.64, 2.08 | |
| 30 | C₂H₅S | H | A | Cl | Cl | 63.50 | 4.71 | 15.1 | — | 63.42 | 4.68 | 15.0 | — | | | quartet, 2.32 | 1740 |
| 31 | H | CH₃ | A | Cl | Cl | 67.40 | 5.08 | 17.0 | — | 67.48 | 4.68 | 16.6 | — | | | | |
| 32 | C₂H₅ | H | A | Cl | Cl | 68.34 | 5.14 | 16.1 | — | 68.03 | 5.02 | 16.1 | — | | | | |
| 33 | NO₂ | H | A | CH₃ | CH₃ | 60.11 | 3.81 | 15.6 | — | 60.27 | 3.74 | 15.5 | — | | | | |
| 34** | (−)C₂H₅O | H | A | Cl | Cl | Same as No. 25 | | | | Same as No. 25 | | | | ([α] = −13.3) | | | |
| 35 | H | H | A | Cl | Cl | 66.55 | 4.53 | 18.2 | — | 65.84 | 4.52 | 17.7 | — | | | quartet, 2.30 | 1740 |
| 36 | NH₂ | H | A | Cl | Cl | 64.42 | 4.60 | 16.7 | — | 64.49 | 4.47 | 16.6 | — | | | quartet, 2.22 | 1740 |
| 37 | Br | H | A | Cl | Cl | 51.41 | 3.18 | 15.9 | (17.9) | 56.12 | 3.48 | 14.41 | (16.24) | 160° at 10⁻⁶ Torr | | quartet, 2.40 | 1745 |

*Values given for —CH₂— of cyclopropane ring
**Refers to optical isomers (see text).

EXAMPLE 38

The biological activity of the new esters of Examples 11 to 37 was examined in a series of tests, the results of which are collected in Table II.

Insecticidal activity and repellency were investigated against the common housefly, *Musca domestica*, and the sheep blowfly, *Lucilia cuprina*. Acaricidal activity was measured against larvae of the Australian cattle tick, *Boophilus microplus*. The methods used were as follows:

(i) Housefly (a) Insecticidal Activity

Tests were carried out using a standard DDT-susceptible strain (WHO/IN/1) of *M. domestica*. The compound was applied in an acetone solution by microsyringe to the dorsum of the thorax of two day old female flies reared from pupae of average weight 2.2–2.5 gm/100 pupae. The adult flies were fed on water and sugar-only diet and maintained at 26° C. and 70% RH. The mortalities were counted at 48 hours after treatment and compared with acetone-treated controls. Flies unable to move or stand normally were considered dead. The $LD_{50}$ value was obtained from a logit computer programme based on three replicates of 10 flies at each dose level. The $LD_{50}$ value for DDT determined under the same conditions was 0.26 μg/fly.

(b) Potentiation

The compound was also tested on the insects described above in conjunction with the potentiator "Sesoxane" by applying 0.5 microlitres of a 1% w/v acetone solution of "Sesoxane" with the compound under test.

The mortalities were counted at 48 hours after treatment and compared with acetone and acetone/potentiator controls.

The $LD_{50}$ value was determined as described above. For DDT, with the same potentiometer the $LD_{50}$ value was 0.24 μg/fly.

About the same levels of potentiation were obtained when "Sesoxane" was replaced by an equal amount of piperonyl butoxide.

(c) Insect Repellency.

Repellency tests were carried out on the same strain of housefly as in the mortality tests. Female flies at least two days old, not previously fed protein, were taken the day before the test, anaesthetized with $CO_2$ and counted into holding containers of twenty flies each. These were supplied with water and solid sucrose. On the day of the tests the food and water were removed in the morning (0900 hr). As the tests were performed only between 1200 hr and 1730 hr, the flies were therefore starved for a minimum of three hours before testing.

The test involved the use of attractant baits to which the candidate compound was applied. These were exposed to the flies and the number of flies landing on each bait counted. The baits consisted of aluminium caps of area 5.94 cm² filled with bakers yeast mixed with water and slightly heated to form a solid surface film.

Eight lots of 20 flies were used in a run in which seven discs were treated with a graded dilution series of the test chemical using acetone as solvent, together with one disc treated with acetone as a control. The concentrations of the compound ranged from 0.031 μg/μl doubling at each level up to 2.0 μg/μl. One hundred microlitres of each solution was pipetted evenly over the surface of each disc and left until the acetone had evaporated.

The flies to be used were released into standard 205 mm×205 mm×255 mm mesh cages and left to acclimatize in the test room maintained at a temperature of 26° C.+1° C. and humidity approximately 60%, for ten minutes before introducing the treated discs into each cage. Before use the discs were marked on the reverse sides and then randomly mixed to avoid bias in counting. In the thirty minute period of the test the number of flies on the surface of each disc was counted in the first and second minute after introducing the baits and thereafter every two minutes.

In this way sixteen counts were obtained for each concentration, the totals of which were than used for a regression analysis of the concentration effect. Also a total number of landings for each concentration was obtained and used for calculation of the Index of Repellency (IR). All replicate tests were carried out with fresh flies and baits, and the compounds were tested in three replicate runs.

The total number of flies counted on each disc for the seven concentration levels was summed and averaged. In the following formula this figure is designated (N), where (C) equals the number of flies counted on the control:

$$\frac{C - N}{C + N} \times 100 = \text{Index of Repellency } (IR)$$

(ii) Sheep Blowfly (a) Insecticidal Activity

The compounds were tested for activity against a dieldrin susceptible strain (LBB) which has been collected before dieldrin usage in the field.

The test compound was applied in acetone solution, 0.5 μl dispensed with a Drummond micropipette to the dorsum of the thorax of 2–3 day old females. Adult flies were fed on water and sugar only and maintained at 25° C. and 60–70% RH. The mortalities were determined after 24 hours. Moribund flies were regarded as dead. The $LD_{50}$ values, in terms of concentration, were interpolated from a probit/log dose graph using a computer program and are converted to μg in Table II.

Comparative $LD_{50}$ figures for DDT and dieldrin are 0.17 and 0.025 μg/insect.

(b) Potentiation

Potentiation with "Sesoxane" was investigated as described above in the housefly tests.

(c) Repellency

Repellency was determined as described above in the housefly tests, except that the baits consisted of an agar gel containing fresh beef blood.

(iii) Cattle Tick

The determinations of mortalities were carried out in packets on 7–14 day old larvae of the cattle tick Boophilus microplus using the method described by B. F. Stone in "Inheritance of resistance to organophosphorus acaricides in the cattle tick Boophilus microplus". *Aust. J. Biol. Sci.* 21, 309–319, (1968).

Mortalities were counted 24 hours after the application of the compounds.

TABLE II

INSECTICIDAL AND ACARICIDAL ACTIVITY

| Example No. Refer to Table I | HOUSEFLY LD$_{50}$ μg/♀ insect | +Sesoxane LD$_{50}$ μg/♀ insect | Repellency Index | OTHER ACTIVITY Blowfly = *Lucilia cuprina* |
|---|---|---|---|---|
| 11 | 0.35 | 0.009 | 77 | |
| 12 | 0.32 | 0.0079 | 86 | |
| 13 | 0.078 | 0.0063 | 66 | Cattle tick larvae 100% kill at 0.1% Blowfly LD$_{50}$ = 0.09 μg/ins. |
| 14 | 0.29 | 0.0011 | 89 | Blowfly repellency 81 |
| 15 | 0.23 | 0.0071 | | |
| 16 | 0.08 | 0.0046 | 45 | Blowfly repellency 50 |
| 17 | 0.18 | 0.0062 | | |
| 18 | 0.29 | 0.007 | | |
| 19 | 0.078 | 0.0016 | | Blowfly repellency 56 |
| 20 | 3.0 | 0.013 | | Blowfly repellency 28 |
| 21 | 0.55 | 0.0028 | | |
| 22 | 0.32 | 0.0095 | | |
| 23 | 0.22 | 0.029 | | |
| 24 | 0.10 | 0.02 | 82 | |
| 25 | >2.0 | 0.03 | | |
| 26 | >2.0 | 0.04 | | |
| 27 | 0.32 | 0.05 | 26 | |
| 28 | 0.20 | 0.007 | | |
| 29 | 1.5 | 0.05 | | |
| 30 | 1.0 | 0.01 | | |
| 31 | >1.0 | 0.061 | 57 | |
| 32 | 0.14 | <0.01 | | |
| 33 | 0.8 | 0.02 | | |
| 34 | 1.0 | 0.023 | | |
| 35 | 1.4 | 0.019 | | |
| 36 | >32 | >32 | | |
| 37 | 0.8 | 0.08 | | |

EXAMPLE 39

The following are examples of insecticidal compositions in accordance with the invention. All parts are by weight.

(a) Spray formulation

The following composition is adapted for spray application.

| | |
|---|---|
| Compound of formula I | 4.0 |
| "Sesoxane" or Piperonyl butoxide | 1.0 |
| Deodorized kerosane | 79.4 |
| Alkylated naphthalene | 16.0 |

(b) Aerosol

The following materials are metered into a suitable 'bomb' container sealed and equipped with a valve in the usual way.

| | |
|---|---|
| Compound of formula I | 3.0 |
| Potentiator | 1.0 |
| Methylene chloride | 10.0 |
| 'Freon 12' | 43.0 |
| 'Freon 11' | 43.0 |

(c) Water dispersable powder

The following powdered composition is intended for dispersing in water for application as a spray.

| | |
|---|---|
| Compound of formula I | 50.0 |
| Synthetic fine silica | 30.0 |
| Alkyl aryl sodium sulphonate | 1.5 |
| Methyl cellulose (15 cp.) | .25 |
| Attapulgite | 8.25 |

We claim:

1. A method for the preparation of phenylacrylic esters of the formula II

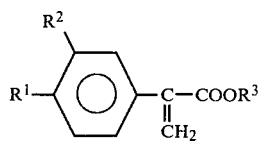

wherein $R^1$ is hydrogen or a methoxy, ethoxy, propoxy, methylthio, ethylthio, propylthio, fluoro, chloro, bromo, methyl, ethyl, nitro or amino group, and $R^2$ is a hydrogen or methyl group;

or $R^1$ and $R^2$ together form a methylenedioxy group; and $R^3$ is a lower alkyl group, which method comprises:

(1) condensing the appropriately substituted phenol acetic ester of formula V

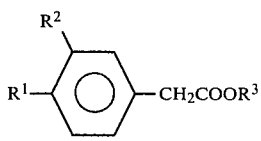

with a di(lower alkyl)oxalate in the presence of a basic catalyst, to produce a solution of an enolate salt of formula IV

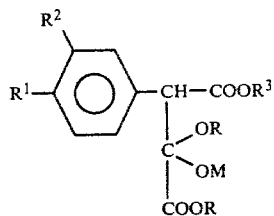

IV wherein R is a lower alkyl group and M is an alkali metal, (2) acidifying the solution of the salt IV to give the corresponding phenyloxaloacetate III

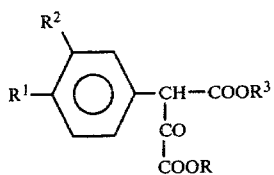

III (3) reacting the compound III with formaldehyde under alkaline conditions to give the corresponding phenyl hydroxymethyl acetate which spontaneously dehydrates to the ester II, each of the steps (1), (2) and (3) being carried out at room temperature.

2. A method as claimed in claim 1 wherein the basic catalyst is an alkali metal alcholate.

3. A method as claimed in claim 2 wherein the alkali metal is sodium.

4. A method as claimed in claim 1 wherein $R^1$ is an ethoxy group and $R^2$ is hydrogen.

5. A method as claimed in claim 1 wherein $R^1$ is nitro and $R^2$ is hydrogen.

6. A method as claimed in claim 1 wherein $R^1$ is chloro and $R^2$ is hydrogen.

7. A method as claimed in claim 1 wherein $R^1$ is bromo and $R^2$ is hydrogen.

8. A method as claimed in claim 1 wherein $R^1$ is methoxy and $R^2$ is hydrogen.

9. A method as claimed in claim 1 wherein $R^1$ and $R^2$ form methylenedioxy.

10. A method as claimed in claim 1 wherein $R^1$ is ethylthio and $R^2$ is hydrogen.

* * * * *

UNITED STATES PATENT AND TRADEMARK OFFICE
CERTIFICATE OF CORRECTION

PATENT NO. : 4,309,350
DATED : January 5, 1982
INVENTOR(S) : George Holan, Reimund Walser It is certified that error appears in the above—identified patent and that said Letters Patent is hereby corrected as shown below:

Claim 1, column 16, line 57, "nol" should read -- nyl --.

Signed and Sealed this

Thirteenth Day of July 1982

[SEAL]

Attest:

Attesting Officer

GERALD J. MOSSINGHOFF
Commissioner of Patents and Trademarks